United States Patent [19]

Boroschewski et al.

[11] Patent Number: 4,537,622
[45] Date of Patent: Aug. 27, 1985

[54] DIURETHANES AND SELECTIVE HERBICIDAL AGENT CONTAINING THEM

[75] Inventors: Gerhard Boroschewski; Friedrich Arndt, both of Berlin, Fed. Rep. of Germany

[73] Assignee: Schering Aktiengesellschaft, Berlin and Bergkamen, Fed. Rep. of Germany

[21] Appl. No.: 157,638

[22] Filed: Jun. 6, 1980

Related U.S. Application Data

[63] Continuation of Ser. No. 44,547, Jun. 1, 1979, abandoned, which is a continuation of Ser. No. 935,106, Aug. 21, 1978, abandoned, which is a continuation of Ser. No. 849,168, Nov. 7, 1977, abandoned.

[30] Foreign Application Priority Data

Nov. 9, 1976 [DE] Fed. Rep. of Germany ....... 2651526

[51] Int. Cl.$^3$ ................ C07C 125/07; C07C 125/075; A01N 37/36; A01N 37/44
[52] U.S. Cl. ....................................... 71/108; 71/111; 560/27; 560/29
[58] Field of Search .................... 560/27, 29; 71/111, 71/108

[56] References Cited

U.S. PATENT DOCUMENTS

| | | | |
|---|---|---|---|
| 3,404,975 | 10/1968 | Wilson et al. | 560/29 |
| 3,546,343 | 12/1970 | Payne et al. | 560/29 |
| 3,551,477 | 12/1970 | Koenig et al. | 560/29 |
| 3,692,820 | 9/1972 | Boroschewski et al. | 560/29 |
| 3,792,994 | 2/1974 | Baker et al. | 560/27 |
| 3,836,570 | 9/1974 | Szabo | 560/29 |
| 3,901,936 | 8/1975 | Boroschewski | 560/27 |
| 3,904,396 | 9/1975 | Boroschewski et al. | 560/29 |

Primary Examiner—Bernard Helfin
Attorney, Agent, or Firm—Michael J. Striker

[57] ABSTRACT

Diurethanes of the general formula

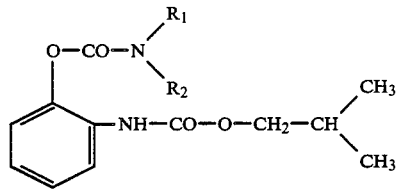

are disclosed, in which $R_1$ is alkyl, alkenyl or haloalkyl, and $R_2$ is phenyl or cyclohexyl or substituted phenyl or cyclohexyl. These compounds show exceptional selective herbicidal activity in particular in tomato cultures, and are most effective in post-emergence treatment.

21 Claims, No Drawings

DIURETHANES AND SELECTIVE HERBICIDAL AGENT CONTAINING THEM

This is a continuation of application Ser. No. 044,547, filed June 1, 1979, now abandoned, which is a continuation of application Ser. No. 935,106, filed Aug. 21, 1978, now abandoned, which in turn was a continuation application of Ser. No. 849,168, filed Nov. 7, 1977, now abandoned.

The invention concerns new diurethanes, a process for the production of these compounds, as well as a selective herbicidal agent containing them, for preferred use in sowing tomatoes.

The selective herbicidal action of diurethanes is known (DT-PS No. 1,567,151). A satisfactory herbicidal action against weeds especially difficult to control, such as amaranthus, and a sufficient selectivity for sowing tomatoes could not be proven for these urethanes until now.

With the above in view it is the object of the present invention to provide a weed control agent which, when used in post emergence, develops besides a general weed action also an action against weed types more difficult to control while being fully compatible with sowing tomatoes.

According to the invention, this problem is solved by a selective herbicidal agent which is characterized by a content of at least one diurethane of the general formula

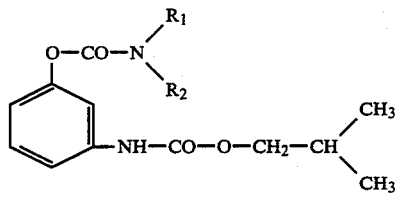

I in which $R_1$ is alkyl, alkenyl or halogen alkyl, and $R_2$ is phenyl, or phenyl or cyclohexyl mono- or poly-substituted, equally or differently, by halogen, trifluoromethyl, alkyl and/or alkoxy.

The diurethanes of the invention are distinguished by a surprisingly great compatibility in particular in sowing tomatoes.

These active substances develop the most favorable action when they are used in post-emergence. The diurethanes of the invention have a broad efficiency.

The herbicidal action extends to many plants, as for example Stellaria, Senecio, Lamium, Centaurea, Amaranthus, Chrysanthemum, Ipomoea, Polygonum and Galium. Besides for sowing tomatoes, there is tolerance for potatoes, cereals, corn, sorghum, and rice.

The quantity used for selective weed control is about 0.5 to 5 kg active substance per hectare.

The diurethanes of the invention can be used either alone, in mixture with one another, or with other active substances.

Depending on the desired purpose, the following herbicidal ingredients, for example, offer themselves to this end; they may optionally be added only just before application of the compounds of the invention: Substituted anilines; substituted aryloxycarboxylic acids and their salts, esters and amides; substituted ethers; substituted arsonic acids and their salts, esters and amides; substituted benzimidazoles; substituted benzisothiazoles; substituted benzothiadiazinone dioxides; substituted benzoxyzines; substituted benzothiazoles; substituted benzothiadiazines; substituted biurets; substituted quinolines; substituted carbamates; substituted aliphatic carboxylic acids and their salts, esters and amides; substituted aromatic carboxylic acids and their salts, esters and amides; substituted carbamoylalkylthio- or dithiophosphates; substituted quinazolines; substituted cycloalkylamidocarbonthiolic acids and their salts, esters and amides; substituted cycloalkylcarbonamido thiazoles; substituted dicarboxylic acids and their salts, esters and amides; substituted dihydrobenzofuranyl sulfonates; substituted disulfides; substituted dipyridylium salts, substituted dithiocarbamates; substituted dithiophosphoric acids and their salts, esters and amides; substituted ureas; substituted hexahydro-1H-carbothioates; substituted hydantoins; substituted hydrazides; substituted hydrazonium salts; substituted isoxazole pyrimidones; substituted imidazoles; substituted isothiazole pyrimidones; substituted ketones; substituted naphthoquinones; substituted aliphatic nitriles; substituted aromatic nitriles; substituted oxadiazoles; substituted oxadiazinones; substituted oxadiazolidinediones; substituted oxadiazinediones; substituted phenols and their salts and esters; substituted phosphonic acids and their salts, esters and amides; substituted phosphonium chlorides; substituted phosphonalkyl glycines; substituted phosphites; substituted phosphoric acids and their salts, esters and amides; substituted piperidines; substituted pyrazoles; substituted pyrazolealkylcarboxylic acids and their salts, esters and amides; substituted pyrazolium salts; substituted pyrazolium alkyl sulfates; substituted pyridazines; substituted pyridazones; substituted pyridinecarboxylic acids and their salts, esters and amides; substituted pyridines; substituted pyridine carboxylates; substituted pyridinones; substituted pyrimidones; substituted pyrrolidine carboxylic acids and their salts, esters and amides; substituted pyrrolidines; substituted arylsulfonic acids and their salts, esters and amides; substituted styrenes; substituted tetrahydro-oxadiazinediones; substituted tetrahydromethanoindenes; substituted tetrahydrodiazolethiones; substituted tetrahydro-thiadiazinethiones; substituted tetrahydro-thiadiazolediones; substituted thiadiazoles; substituted aromatic thiocarboxylic acid amides; substituted thiocarboxylic acids and their salts, esters and amides; substituted thiolcarbamates; substituted thiophosphoric acids and their salts, esters and amides; substituted triazines; substituted triazoles; substituted uracils and substituted uretindiones.

Besides other additions may be used as well, for example non-phytotoxic additives which in herbicides may give a synergistic effect, such as wetting agents, emulsifiers, solvents and oily additions.

Appropriately the characterized active substances or their mixtures are employed in the form of preparations, such as powders, scatters, granulated materials, solutions, emulsions or suspensions, with addition of liquid and/or solid vehicles or diluents and possibly wetting, bonding, emulsifying and/or dispersing aids.

Suitable liquid vehicles are, for example, water, aliphatic and aromatic hydrocarbons, such as benzene, toluene, xylene, cyclohexanone, isophorone, dimethylsulfoxide, dimethyl formamide, also mineral oil fractions.

As solid vehicles are suitable mineral earths, for example, siliceous clay, silica gel, talc, kaolin, attaclay, limestone, silica, and plant products, e.g. flours.

Among surface-active substances should be named, for example, calcium-lignin sulfonate, polyoxyethylene alkyl-phenyl ether, naphthalene sulfonic acids and their salts, phenol-sulfonic acids and their salts, formaldehyde condensates, fatty alcohol sulfates and substituted benzene-sulfonic acids and their salts.

The proportion of active ingredient(s) in the various preparations may vary within wide limits. As an example, the agents contain about 10 to 80 weight percent active ingredients, about 90 to 20 weight percent liquid or solid vehicles, and possibly up to 20 weight percent surface-active substances.

The spreading of the agents can be done in the usual manner, e.g. with water as vehicle in spray solution quantities of about 100 to 1000 liters per hectare. Use of the agents in the so-called "Low Volume" or "Ultra Low Volume" processes is as possible as their application in the form of so-called micro-granulates.

Outstanding for superior selective herbicidal action in particular in sowing tomatoes are among the diurethanes of the invention preferably those which correspond to the above stated general formula, wherein $R_1$ is $C_1$-$C_4$ alkyl, $C_2$-$C_4$ alkenyl, halogen-$C_1$-$C_4$ alkyl and $R_2$ is phenyl, $C_1$-$C_3$ alkylphenyl, $C_1$-$C_3$ alkoxyphenyl, chlorophenyl, dichlorophenyl, trifluoromethyl or cyclohexyl.

Advantageously there are distinguished among these those compounds where $R_1$ is ethyl, propyl, isopropyl, butyl, isobutyl, chloroethyl, bromoethyl, allyl, and $R_2$ is cyclohexyl, phenyl, methylphenyl, dimethylphenyl, chlorophenyl, dichlorophenyl, chloro-methylphenyl, trifluoromethylphenyl, methoxyphenyl, fluorophenyl, ethylphenyl, methoxy-methylphenyl.

The diurethanes not previously known in the literature can be produced for example, by (a) reacting the chloroformic acid ester of 3-hydroxycarbanilic acid isobutyl ester

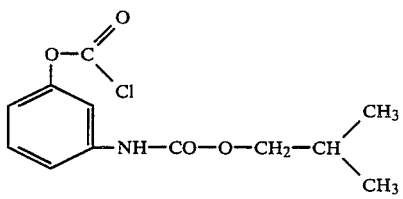

with amines of the general formula

in the presence of an acid acceptor, for example, with addition of excess amine or an inorganic base, as for example soda lye, sodium carbonate, potassium carbonate, or a tertiary organic base, as for example triethylamine, or (b) letting 3-hydroxycarbanilic acid isobutyl ester

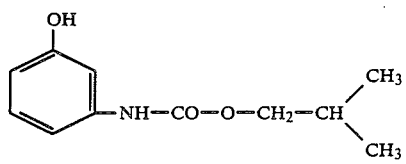

react in the presence of a tertiary organic base, as for example triethylamine or pyridine, or as alkali salts with carbamoyl chlorides of the general formula

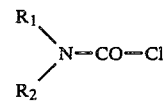

at temperatures of 0° to 100° C., or (c) hydrogenating compounds of the general formula

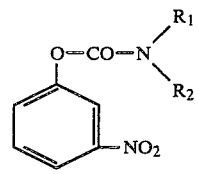

catalytically, for example with the use of nickel in methanol to the corresponding amine and subsequently reacting with compounds of the general formula

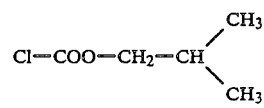

in the presence of an acid acceptor, for example an inorganic base, such as soda lye, sodium carbonate or potassium carbonate, or a tertiary organic base, as for example triethylamine, to form the desired process products, and then isolating them in the usual manner, $R_1$ and $R_2$ having the above meaning.

The following example explains the production of the diurethanes according to the invention.

EXAMPLE 1

4-Chloro-N-methylcarbanilic acid (3-(2-methylpropoxycarbonylamino)-phenyl)ester

A solution of 14.2 g (0.1 mole) 4-chloro-N-methylaniline in 100 ml acetic acid ethyl ester is mixed with 50 ml water. Then a solution of 27.2 g (0.1 mole) chloroformic acid-3-(2-methylpropoxycarbonylamino)-phenyl ester in 100 ml acetic acid ethyl ester and simultaneously a solution of 13.8 g (0.1 mole) potassium carbonate in 50 ml water is added in drops within 20 minutes while agitating and cooling to 10° to 15° C. Agitation is continued at 15° C. for another 30 minutes. Then the organic phase is separated, washing at 0° C. with dilute soda lye, dilute hydrochloric acid and water. Drying with magnesium sulfate is followed by evaporation under reduced pressure. Recrystallization from acetic acid ethyl ester/pentane.

Analysis: Calculated: C, 60.56%; H, 5.62%; Cl, 9.41%; N, 7.44%. Found: C, 60.67%; H, 5.84%; Cl, 9.49%; N, 7.44%.

In analogous manner the following diurethanes to be used according to the invention can be produced.

| Name of Compound | Physical Constant | |
|---|---|---|
| N—methylcarbanilic acid-(3-(2-methylpropoxy-carbonylamino)-phenyl) ester | M.p. | 90–92° C. |
| N—ethylcarbanilic acid-(3-(2-methylpropoxy-carbonylamino)-phenyl) ester | M.p. | 107–108° C. |
| N—butylcarbanilic acid-(3-(2-methylpropoxy-carbonylamino)-phenyl) ester | $n_D^{20}$ | 1.5391 |
| N—allylcarbanilic acid-(3-(2-methylpropoxy-carbonylamino)-phenyl) ester | M.p. | 67–69° C. |
| N—propylcarbanilic acid-(3-(2-methylpropoxy-carbonylamino)-phenyl) ester | M.p. | 61–62° C. |
| N—ethyl-3-methylcarbanilic acid-(3-(2-methylpropoxycarbonylamino)-phenyl) ester | M.p. | 90–92° C. |
| N—ethyl-3-chlorocarbanilic acid-(3-(2-methylpropoxycarbonylamino)-phenyl) ester | M.p. | 95–97° C. |
| N—(1-methylethyl)-carbanilic acid-(3-(2-methylpropoxycarbonylamino)-phenyl) ester | M.p. | 116–118° C. |
| 3-Chloro-N—methylcarbanilic acid-(3-(2-methylpropoxycarbonylamino)-phenyl) ester | M.p. | 102–104° C. |
| 3,N—dimethylcarbanilic acid-(3-(2-methylpropoxycarbonylamino)-phenyl) ester | $n_D^{20}$ | 1.5479 |
| N—ethyl-4-chlorocarbanilic acid-(3-(2-methylpropoxycarbonylamino)-phenyl) ester | M.p. | 87–89° C. |
| 4,N—dimethylcarbanilic acid-(3-(2-methylpropoxycarbonylamino)-phenyl) ester | $n_D^{20}$ | 1.5547 |
| 4-Ethyl-N—methylcarbanilic acid-(3-(2-methylpropoxycarbonylamino)-phenyl) ester | $n_D^{20}$ | 1.5529 |
| 3,4-Dichloro-N—methylcarbanilic acid-(3-(2-methylpropoxycarbonylamino)-phenyl) ester | $n_D^{20}$ | 1.5691 |
| N—ethyl-4-methylcarbanilic acid-(3-(2-methylpropoxycarbonylamino)-phenyl) ester | M.p. | 82–83° C. |
| N—Ethyl-3,4-dichlorocarbanilic acid-(3-(2-methylpropoxycarbonylamino)-phenyl) ester | M.p. | 94–96° C. |
| 4-Chloro-N—methylcarbanilic acid-(3-(2-methylpropoxycarbonylamino)-phenyl) ester | M.p. | 65–66° C. |
| N—Ethyl-2-methylcarbanilic acid-(3-(2-methylpropoxycarbonylamino)-phenyl) ester | M.p. | 101–103° C. |
| N—(2-methylpropyl)-carbanilic acid-(3-(2-methylpropoxycarbonylamino)-phenyl) ester | M.p. | 82–84° C. |
| 2,N—dimethylcarbanilic acid-(3-(2-methylpropoxycarbonylamino)-phenyl) ester | M.p. | 122° C. |
| N—(2-bromethyl)-carbanilic acid-(3-(2-methylpropoxycarbonylamino)-phenyl) ester | M.p. | 82–83° C. |
| N—(2-bromethyl)-3-chlorocarbanilic acid-(3-(2-methylpropoxycarbonylamino)-phenyl) ester | M.p. | 60–63° C. |
| N—(2-chlorethyl)-carbanilic acid-(3-(2-methylpropoxycarbonylamino)-phenyl) ester | M.p. | 95–96° C. |
| 3-Chloro-N—(2-chlorethyl)-carbanilic acid-(3-(2-methylpropoxycarbonylamino)-phenyl ester | $n_D^{20}$ | 1.5514 |
| N—ethyl-cyclohexylcarbamic acid-(3-(2-methyl-propoxycarbonylamino)-phenyl) ester | M.p. | 107–110° C. |
| N—cyclohexyl-methylcarbamic acid-(3-(2-methylpropoxycarbonylamino)-phenyl) ester | M.p. | 122–123° C. |
| N—(2-chloroethyl)-cyclohexylcarbamic acid-(3-(2-methylpropoxycarbonylamino)-phenyl) ester | $n_D^{20}$ | 1.5231 |

These compounds are soluble in acetone, cyclohexanone, acetic acid ethyl ester, isophorone, tetrahydrofurane, dioxane, dimethylformamide, dimethyl sulfoxide, hexamethyl phosphoric acid triamide, and practically insoluble in water and light gasoline.

The following examples serve to explain the mode of action of the diurethanes to be used according to the invention.

EXAMPLE 2

In the greenhouse, the compounds to be used according to the invention, listed in the table, were sprayed in a quantity of 5 kg active substance per hectare on *Sinapis alba* as test plant in post-emergence. Three weeks after the treatment, the result was rated, with
0 = no action and
4 = destruction of the plant.
As can be seen from the table, as a rule destruction of the test plant was achieved.

| Name of Compound | Post-emergence *Sinapis alba* |
|---|---|
| N—methylcarbanilic acid-(3-(2-methyl-propoxycarbonylamino)-phenyl) ester | 4 |
| N—ethylcarbanilic acid-(3-(2-methyl-propoxycarbonylamino)-phenyl) ester | 4 |
| N—butylcarbanilic acid-(3-(2-methyl-propoxycarbonylamino)-phenyl) ester | 4 |
| N—allylcarbanilic acid-(3-(2-methyl-propoxycarbonylamino)-phenyl) ester | 4 |
| N—propylcarbanilic acid-(3-(2-methyl-propoxycarbonylamino)-phenyl) ester | 4 |
| N—ethyl-3-methylcarbanilic acid-(3-(2-methylpropoxycarbonylamino)-phenyl) ester | 4 |
| N—ethyl-3-chlorocarbanilic acid-(3-(2-methyl-propoxycarbonylamino)-phenyl) ester | 4 |
| N—(1-methylethyl)-carbanilic acid-(3-(2-methyl-propoxycarbonylamino)-phenyl) ester | 4 |
| 3-Chloro-N—methylcarbanilic acid-(3-(2-methyl-propoxycarbonylamino)-phenyl) ester | 4 |
| 3,N—dimethylcarbanilic acid(3-(2-methylprop-oxycarbonylamino)-phenyl) ester | 4 |
| N—ethyl-4-chlorocarbanilic acid-(3-(2-methyl-propoxycarbonylamino)-phenyl) ester | 4 |
| 4,N—dimethylcarbanilic acid-(3-(2-methylprop-oxycarbonylamino)-phenyl) ester | 4 |
| 4-Ethyl-N—methylcarbanilic acid-(3-(2-methyl-propoxycarbonylamino)-phenyl) ester | 4 |
| 3,4-Dichloro-N—methylcarbanilic acid-(3-(2-methylpropoxycarbonylamino)-phenyl ester | 4 |
| N—ethyl-4-methylcarbanilic acid-(3-(2-methyl-propoxycarbonylamino)-phenyl) ester | 4 |
| N—ethyl-3,4-dichlorocarbanilic acid-(3-(2-methylpropoxycarbonylamino)-phenyl) ester | 4 |
| 4-Chloro-N—methylcarbanilic acid-(3-(2-methyl-propoxycarbonylamino)-phenyl) ester | 4 |
| N—ethyl-cyclohexylcarbamic acid-(3-(2-methyl-propoxycarbonylamino)-phenyl) ester | 4 |
| N—cyclohexyl-methylcarbamic acid-(3-(2-methylpropoxycarbonylamino)-phenyl) ester | 4 |
| N—(2-chloroethyl)-cyclohexylcarbamic acid-(3-(2-methylpropoxycarbonylamino)-phenyl) ester | 4 |

EXAMPLE 3

In the greenhouse, the plants listed below were treated in post-emergence with a quantity of 3 kg active substance per hectare. As comparison agent was used 3-(methoxycarbonylaminophenyl)-N-(β-methyl-phenyl)carbamate (according to German Pat. No. 1,567,151). The plants were in the immature stage. The agents were spread as emulsions. The quantity of liquid applied was 500 liter/hectare. After two weeks, the result of the treatment was rated.
0 = total destruction
10 = no damage.

As is evident from the table, the compounds to be used according to the invention achieved a good weed action at excellent compatibility with sowing tomatoes, while the comparison agent harmed the crop plant, at lesser action.

POST EMERGENCE kg active

-continued

POST EMERGENCE

| Compounds | sub-stance/ha | Sowing tomato | Stel-laria m. | Senecio v. | Matri-caria ch. | Lamium a. | Cen-taurea c. | Amaran-thus r. | Gal-ium a. | Chrysan-themum a. | Ipo-moea p. | Poly-gonum l. | A-vena f. | Alo-pecur-us m. | Echino-chloa c.g. | Se-taria i. | Digi-taria s. |
|---|---|---|---|---|---|---|---|---|---|---|---|---|---|---|---|---|---|
| N—methylcarbanilic acid-(3-(2-methylpropoxy-carbonylamino)-phenyl) ester | 3 | 10 | 0 | 0 | 0 | 0 | 0 | 0 | 0 | 0 | 0 | 0 | 2 | 3 | 2 | 0 | 0 |
| N—ethylcarbanilic acid-(3-(2-methyl-propoxycarbonylamino)-phenyl) ester | 3 | 10 | 0 | 0 | 0 | 0 | 0 | 0 | 0 | 0 | 0 | 0 | 3 | 1 | 1 | 0 | 1 |
| N—butylcarbanilic acid-(3-(2-methyl-propoxycarbonylamino)-phenyl) ester | 3 | — | 0 | 0 | 0 | 0 | 0 | 0 | 0 | 0 | 0 | 0 | 3 | 3 | — | 0 | 2 |
| N—allylcarbanilic acid-(3-(2-methyl-propoxycarbonylamino)-phenyl) ester | 3 | 10 | 0 | 0 | 0 | 0 | 0 | 0 | 0 | 0 | 0 | 0 | 4 | 1 | 1 | 0 | 0 |
| N—propylcarbanilic acid-(3-(2-methyl-propoxycarbonylamino)-phenyl) ester | 3 | — | 0 | 0 | 0 | 0 | 0 | 0 | 0 | 0 | 0 | 0 | 0 | 4 | 0 | 0 | 0 |
| Ethyl-3-methylcarbanilic acid-(3-(2-methyl-Propoxycarbonylamino)-phenyl) ester | 3 | 10 | 0 | 0 | 0 | 0 | 0 | 0 | 0 | 0 | 0 | — | 0 | 3 | — | 3 | 2 |
| N—ethyl-3-chlorocarbanilic acid-(3-(2-methylpropoxycarbonylamino)-phenyl) ester | 3 | 10 | 0 | 0 | 0 | 0 | 0 | 0 | 0 | 0 | 0 | 0 | 5 | — | 3 | 1 | 0 |
| 3-Chloro-N—methylcarbanilic acid-(3-(2-methylpropoxycarbonylamino)-phenyl) ester | 3 | 10 | 0 | 0 | 0 | 0 | 0 | 0 | 0 | 0 | 1 | 0 | 5 | — | 3 | 2 | 0 |
| 3,N—dimethylcarbanilic acid-(3-(2-methyl-propoxycarbonylamino)-phenyl) ester | 3 | 10 | 0 | 0 | 0 | 0 | 1 | 0 | 0 | 0 | 0 | 0 | 5 | 3 | 2 | 1 | 0 |
| N—ethyl-4-chlorocarbanilic acid-(3-(2-methyl-propoxycarbonylamino)-phenyl) ester | 3 | 10 | 0 | 0 | 0 | 0 | 0 | 0 | 0 | 0 | 1 | — | 2 | 3 | 5 | 0 | 1 |
| 4-Ethyl-N—methylcarbanilic acid-(3-(2-methyl-propoxycarbonylamino)-phenyl) ester | 3 | 10 | 0 | 0 | 0 | 0 | 0 | 0 | 0 | 0 | 3 | 0 | — | 5 | — | 3 | 2 |
| 3,4-Dichloro-N—methylcarbanilic acid-(3-(2-methylpropoxycarbonylamino)-phenyl) ester | 3 | 10 | 0 | 0 | 0 | 0 | 0 | 0 | 0 | 0 | 0 | 0 | 4 | 5 | 2 | 0 | 1 |
| N—ethyl-4-methylcarbanilic acid-(3-(2-methyl-propoxycarbonylamino)-phenyl) ester | 3 | 10 | 0 | 0 | 0 | 0 | 0 | 0 | 0 | 0 | 2 | 0 | 5 | — | 3 | 0 | 1 |
| N—ethyl-3,4-dichlorocarbanilic acid-(3-(2-methylpropoxycarbonylamino)-phenyl) ester | 3 | 10 | 0 | 0 | 0 | 0 | 0 | 0 | 0 | 0 | 0 | 0 | 0 | — | 3 | 3 | — |
| 4-Chloro-N—methylcarbanilic acid-(3-(2-methylpropoxycarbonylamino)-phenyl) ester | 3 | 10 | 0 | 0 | 0 | 0 | 0 | 0 | 0 | 0 | 0 | 0 | 1 | 3 | 1 | 0 | 3 |
| Comparison Agent | | | | | | | | | | | | | | | | | |
| 3-(Methoxycarbonylaminophenyl)-N—(3'-methyl-phenyl) carbamate | 3 | 0 | 1 | 2 | 0 | 0 | 0 | 4 | 0 | 3 | 0 | 4 | 10 | 8 | 8 | 0 | 2 |
| UNTREATED | | 10 | 10 | 10 | 10 | 10 | 10 | 10 | 10 | 10 | 10 | 10 | 10 | 10 | 10 | 10 | 10 |

0 = Total destruction/10 = no damage

We claim:

1. Diurethanes of the general formula

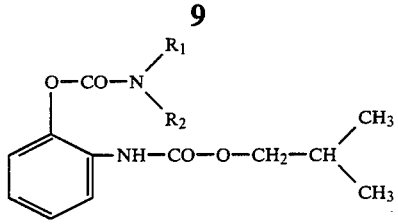

in which

R₁ is alkyl, alkenyl or halogen alkyl and

R₂ is phenyl, or phenyl or cyclohexyl mono- or polysubstituted, equally or differently, by halogen, trifluoromethyl, alkyl and/or alkoxy.

2. A compound as set forth in claim 1, in which R₁ is C₁–C₄-alkyl, C₂–C₄-alkenyl, halogen-C₁–C₄-alkyl and R₂ is phenyl, C₁–C₃-alkylphenyl, C₁–C₃-alkoxyphenyl, chlorophenyl, dichlorophenyl, trifluoromethylphenyl or cyclohexyl.

3. A compound as defined in claim 1 which is N-ethyl-3-methylcarbanilic acid-(3-(2-methylpropoxycarbonylamino)-phenyl)ester.

4. A compound as defined in claim 1 which is N-ethyl-3-chlorocarbanilic acid-(3-(2-methylpropoxycarbonylamino)-phenyl)ester.

5. A compound as defined in claim 1 which is N-(1-methylethyl)-carbanilic acid-(3-(2-methylpropoxycarbonylamino)-phenyl)ester.

6. A compound as defined in claim 1 which is 3-chloro-N-methylcarbanilic acid-(3-(2-methylpropoxycarbonylamino)-phenyl)ester.

7. A compound as defined in claim 1 which is 3,N-dimethylcarbanilic acid-(3-(2-methylpropoxycarbonylamino)phenyl)ester.

8. A compound as defined in claim 1 which is N-ethyl-4-chlorocarbanilic acid-(3-(2-methylpropoxycarbonylamino)-phenyl)ester.

9. A compound as defined in claim 1 which is 4,N-dimethylcarbanilic acid-(3-(2-methylpropoxycarbonylamino)-phenyl)ester.

10. A compound as defined in claim 1 which is 4-ethyl-N-methylcarbanilic acid-(3-(2-methylpropoxycarbonylamino)-phenyl)ester.

11. A compound as defined in claim 1 which is 3,4-dichloro-N-methylcarbanilic acid-(3-(2-methylpropoxycarbonylamino)-phenyl)ester.

12. A compound as defined in claim 1 which is N-ethyl-4-methylcarbanilic acid-(3-(2-methylpropoxycarbonylamino)-phenyl)ester.

13. A compound as defined in claim 1 which is N-ethyl-3,4-dichlorocarbanilic acid-(3-(2-methylpropoxycarbonylamino)-phenyl)ester.

14. A compound as defined in claim 1 which is 4-chloro-N-methylcarbanilic acid-(3-(2-methylpropoxycarbonylamino)-phenyl)ester.

15. A compound as defined in claim 1 which is N-ethyl-2-methylcarbanilic acid-(3-(2-methylpropoxycarbonylamino)-phenyl)ester.

16. A compound as defined in claim 1 which is N-(2-methylpropyl)-carbanilic acid-(3-(2-methylpropoxycarbonylamino)-phenyl)ester.

17. A compound as defined in claim 1 which is 2,N-dimethylcarbanilic acid-(3-(2-methylpropoxycarbonylamino)-phenyl)ester.

18. A compound as defined in claim 1 which is N-ethyl-cyclohexylcarbamic acid-(3-(2-methylpropoxycarbonylamino)-phenyl)ester.

19. A compound as defined in claim 1 which is N-cyclohexyl-methylcarbamic acid-(3-(2-methylpropoxycarbonylamino)-phenyl)ester.

20. A compound as defined in claim 1 which is N-(2-chloroethyl)-cyclohexylcarbamic acid-(3-(2-methylpropoxycarbonylamino)-phenyl)ester.

21. A herbicidal composition comprising about 10 to 80 weight-% of a compound as defined in claim 1 and about 90 to 20 weight-% liquid or solid carrier material administered as a spray solution.

* * * * *